United States Patent [19]

Pretzer et al.

[11] 4,239,704

[45] Dec. 16, 1980

[54] PROCESS FOR PRODUCING ACETALDEHYDE

[75] Inventors: Wayne R. Pretzer; Thaddeus P. Kobylinski, both of Gibsonia; John E. Bozik, Pittsburgh, all of Pa.

[73] Assignee: Gulf Research & Development Company, Pittsburgh, Pa.

[21] Appl. No.: 42,330

[22] Filed: May 25, 1979

Related U.S. Application Data

[63] Continuation-in-part of Ser. No. 957,130, Nov. 2, 1978, and Ser. No. 936,717, Aug. 25, 1978.

[51] Int. Cl.$^3$ ............................................. C07C 47/06
[52] U.S. Cl. .................................................. 568/487
[58] Field of Search ............................. 568/909, 882; 260/601 R

[56] References Cited

U.S. PATENT DOCUMENTS

| 3,285,948 | 11/1966 | Butler | 260/601 R |
| 3,356,734 | 12/1967 | Kuraishi | 260/601 R |
| 3,576,881 | 4/1971 | Senn | 260/604 HF |
| 3,996,288 | 12/1976 | Yukata et al. | 260/599 |

Primary Examiner—Werren B. Lone

[57] ABSTRACT

A process for selectively producing acetaldehyde which comprises introducing into a reaction zone (1) methanol, (2) hydrogen, (3) carbon monoxide, (4) a cobalt carbonyl, a hydrido cobalt carbonyl or a cobalt-containing material convertible to a cobalt carbonyl or a hydrido cobalt carbonyl, (5) an arsenic or antimony base ligand and (6) an iodine compound and then subjecting the contents of said reaction zone to an elevated temperature and an elevated pressure for a time sufficient to convert methanol to acetaldehyde.

22 Claims, No Drawings

PROCESS FOR PRODUCING ACETALDEHYDE

This application is a continuation-in-part application of our U.S. Patent Application Ser. No. 957,130, filed Nov. 2, 1978 for CRITICAL I/Co RATIOS FOR THE SELECTIVE PRODUCTION OF ACETALDEHYDE IN A CARBONYLATION PROCESS and of our U.S. Patent Application Ser. No. 936,717, filed Aug. 25, 1978 for A PROCESS FOR SELECTIVE FORMATION OF ACETALDEHYDE FROM METHANOL, HYDROGEN AND CARBON MONOXIDE USING A COBALT SOURCE IN COMBINATION WITH AN ARSENIC OR ANTIMONY BASE LIGAND AND AN IODINE PROMOTER.

BACKGROUND OF THE INVENTION

1. Field of the Invention

This invention is directed to a process for selectively producing acetaldehyde which comprises introducing into a reaction zone (1) methanol, (2) hydrogen, (3) carbon monoxide, (4) a cobalt carbonyl, a hydrido cobalt carbonyl or a cobalt-containing material convertible to a cobalt carbonyl or a hydrido cobalt carbonyl, (5) an arsenic or antimony base ligand and (6) an iodine compound and then subjecting the contents of said reaction zone to an elevated temperature and an elevated pressure for a time sufficient to convert methanol to acetaldehyde.

2. Description of the Prior Art

The synthesis of oxygenated hydrocarbons, such as aldehydes, alcohols, etc., by reacting methanol with synthesis gas (hydrogen and carbon monoxide) is not a new concept. Processes are available for producing a wide spectrum of oxygen-containing hydrocarbons, such as alcohols, aldehydes, ketones, esters, ethers and fatty acids of almost any chain length and degree of saturation. The relative amount or extent to which one or more of the above-described products is obtained is determined and/or controlled by the type catalyst used in the reaction. Catalysts which have been used in the past to produce aldehydes, alcohols, etc., are those selected from iron, cobalt, nickel, zinc and the like on a support, either alone or in combination with one or more promoter(s).

The conversion of an alcohol, for example, methanol, to an aldehyde, such as acetaldehyde, containing one carbon atom more than the original alcohol is normally a tedious and time-consuming procedure involving a series of steps. Additionally, catalysts which possess acceptable activity generally tend to give a wide spectrum of products, for example, hydrocarbons and oxygenated hydrocarbons having a broad distribution of carbon atoms. This not only complicates the separation and recovery of desired products, but results in reduced yield of said desired products and erosion of reactants in the production of undesirable products.

The reaction of methanol with hydrogen and carbon monoxide to produce acetaldehyde is appreciated and disclosed by the prior art. However, most known processes produce an undesirably large mixture of alcohols, ketones and carboxylic acids in addition to the desired aldehyde.

U.S. Pat. No. 3,356,734, issued to Kurahhi et al, on Dec. 5, 1967, entitled "Process for the Production of Acetaldehyde", teaches a process for the production of acetaldehyde in two steps. In the first step, methanol, hydrogen and carbon monoxide are contacted with a cobalt catalyst and a halogen promoter to form a product predominating in acetals. The cobalt catalyst described is selected from cobalt salts which are soluble in methanol. In particular, preferred soluble salts include cobalt acetate, cobalt bromide, chlorate, chloride, iodide, sulfide and the like. The halogen promoter is selected from iodine, bromine, chlorine and the like. In the second step, the acetals so produced are contacted with a second distinct catalyst system to hydrolyze the acetals to acetaldehyde and methanol. Maximum possible selectivity to acetaldehyde is from about 17 to about 38 mol percent of the converted methanol.

Another process for producing aldehydes is disclosed in U.S. Pat. No. 3,996,288, entitled "Method of Producing Aldehydes by Hydroformylation", issued to Yukata et al, on Dec. 7, 1976. Particularly, the reference relates to a process for preparing phenylacetaldehyde by contacting hydrogen, carbon monoxide, an amide of a carboxylic acid and benzyl chloride at elevated temperature and pressure in the presence of a carbonylation catalyst, for example, dicobalt octacarbonyl. The reference, however, fails to appreciate a process for the selective formation of acetaldehyde from methanol, hydrogen and carbon monoxide.

SUMMARY OF THE INVENTION

The present invention relates to a process for selectively producing acetaldehyde which comprises introducing into a reaction zone (1) methanol, (2) hydrogen, (3) carbon monoxide, (4) a cobalt carbonyl, a hydrido cobalt carbonyl or a cobalt-containing material convertible to a cobalt carbonyl or a hydrido cobalt carbonyl, (5) an arsenic or antimony base ligand and (6) an iodine compound and then subjecting the contents of said reaction zone to an elevated temperature and an elevated pressure for a time sufficient to convert methanol to acetaldehyde.

From the above it can be seen that for the purposes of the process defined and claimed herein six separate and distinct entities are introduced into a reaction zone prior to subjecting them to an elevated temperature and elevated pressure sufficient to obtain acetaldehyde. Of these the cobalt entity, the arsenic or antimony base ligand and the iodine entity require further elucidation.

The cobalt entity is defined as being a cobalt carbonyl, a hydrido cobalt carbonyl or a cobalt-containing material convertible to a cabalt carbonyl or a hydrido cobalt carbonyl. By "cobalt carbonyl" we intend to define a compound containing only cobalt and carbon monoxide, such as $Co_2(CO)_8$ or $C_4(CO)_{12}$. By "hydrido cobalt carbonyl" we intend to define a compound containing only cobalt, carbon monoxide and hydrogen, such as $HCo(CO)_4$. By "cobalt-containing material convertible to a cobalt carbonyl or a hydrido cobalt carbonyl" we intend to define any material which when mixed with hexane and subjected to 4000 pounds per square inch (27.6 MPa) in an atmosphere containing hydrogen and carbon monoxide in a molar ratio of 1:1 at 150° to 200° C. for a period of three hours will result in the formation of a cobalt carbonyl, a hydrido cobalt carbonyl or mixtures thereof. Specific examples of a cobalt-containing material so convertible to a cobalt carbonyl or a hydrido cobalt carbonyl include cobalt (II) sulfate, cobalt oxide ($Co_3O_4$), cobalt (II) tetrafluoroborate, cobalt (II) acetate, cobalt (II) oxalate, cobalt (II) propionate, cobalt (II) octoate, cobalt (II) butyrate, cobalt (II) benzoate, cobalt (II) valerate, cobalt (II) formate, cobalt (II) cyclohexanebutyrate, cobalt (II)

2-ethylhexoate, cobalt (II) gluconate, cobalt (II) lactate, cobalt (II) naphthenate, cobalt (II) oleate and cobalt (II) citrate.

The arsenic or antimony base ligand can be defined by the following formula:

wherein X is a member selected from the group consisting of trivalent arsenic or trivalent antimony; and $R_1$, $R_2$ and $R_3$ are either alike or different members selected from the group consisting of saturated or unsaturated, straight or branched chain alkyl radicals having from one to 24 carbon atoms, preferably from one to 10 carbon atoms; alkenyl radicals having from two to 30 carbon atoms, preferably from two to 20 carbon atoms; cycloalkyl radicals having from three to 40 carbon atoms, preferably from three to 30 carbon atoms; aryl radicals having from six to 20 carbon atoms, preferably from six to 10 carbon atoms; and aralkyl and alkaryl radicals having from six to 40 carbon atoms, preferably from six to 30 carbon atoms, with the provision that at least one R group is aryl, aralkyl or alkaryl.

Arsenic and antimony base ligands which are suitable for use herein include the following:

triphenyl arsine
tri-p-tolyl arsine
tri-m-tolyl arsine
tri-o-tolyl arsine
tri-p-cumyl arsine
tri-(4-ethylphenyl) arsine
diphenyl methyl arsine
diphenyl ethyl arsine
diphenyl propyl arsine
diphenyl butyl arsine
diphenyl cyclohexyl arsine
diphenyl benzyl arsine
methyl di(p-tolyl) arsine
diphenyl vinyl arsine
dimethyl phenyl arsine
dimethyl (p-tolyl) arsine dimethyl (p-cumyl) arsine
diethyl phenyl arsine
dibutyl phenyl arsine
dicyclohexyl (p-tolyl) arsine
methyl ethyl phenyl arsine
methyl phenyl (p-tolyl) arsine
diphenyl eicosyl arsine
dieicosyl phenyl arsine
dibenzyl phenyl arsine
divinyl phenyl arsine
methyl dinaphthyl arsine
dimethyl naphthyl arsine
triphenyl stibine
tri-p-tolyl stibine
tri-m-tolyl stibine
tri-o-tolyl stibine
tri-p-cumyl stibine
tri-(4-ethylphenyl) stibine
diphenyl methyl stibine
diphenyl ethyl stibine
diphenyl propyl stibine
diphenyl butyl stibine
diphenyl cyclohexyl stibine
diphenyl benzyl stibine
methyl di(p-tolyl) stibine
diphenyl vinyl stibine
dimethyl phenyl stibine
dimethyl (p-tolyl) stibine
dimethyl (p-cumyl) stibine
diethyl phenyl stibine
dibutyl phenyl stibine
dicyclohexyl (p-tolyl) stibine
methyl ethyl phenyl stibine
methyl phenyl (p-tolyl) stibine
diphenyl eicosyl stibine
dieicosyl phenyl stibine
dibenzyl phenyl stibine
divinyl phenyl stibine
methyl dinaphthyl stibine, or
dimethyl naphthyl stibine and mixtures thereof.

Any source of iodine which is capable of disassociating, that is, ionizing to form free iodide ions in the reaction medium, can be used in the present invention. Illustrative examples of iodine compounds especially suitable for use herein include iodine, potassium iodide, calcium iodide, sodium iodide, lithium iodide, hydrogen iodide, methyl iodide, ethyl iodide, etc.

The relative amounts of carbon monoxide and hydrogen employed can be varied over a wide range. However, in general, the molar ratio range of carbon monoxide to hydrogen is from about 1:10 to about 10:1, especially from about 1:3 to about 3:1; however, conventional synthesis gas (mixtures of carbon monoxide and hydrogen) with a molar ratio of about 1:1 is convenient and satisfactory for the process herein. It is to be noted that molar ratios outside the aforestated ratio ranges can be employed herein. Compounds or reaction mixtures which give rise to the formation of carbon monoxide and hydrogen under the reaction conditions defined herein can be used instead of mixtures comprising carbon monoxide and hydrogen which are used in the preferred embodiments of this invention.

The cobalt entity and the arsenic and/or antimony base ligand are introduced into the reaction zone in molar ratios, based on the elements cobalt and arsenic and/or antimony, respectively, ranging from about 20:1 to about 1:10, preferably from about 10:1 to about 1:5. The cobalt entity and the iodine entity are introduced into the reaction zone in molar ratios, based on the elements cobalt and iodine, respectively, ranging from about 100:1 to about 1:2, preferably from about 10:1 to about 1:1. Based on the methanol introduced into the system, the weight percent of combined cobalt, arsenic and/or antimony entities and iodine, in their elemental form, can range from about 0.01 to about 10 percent, preferably from about 0.1 to about five percent.

The process defined herein can be carried out either in a batch operation or by passing the reactants continuously through a reaction zone. In each case the reactor is provided with agitation means and the pressure is maintained therein by the addition of hydrogen and carbon monoxide as required. In order to facilitate introduction of the cobalt, arsenic and/or antimony and iodine entities into the reaction zone and/or to facilitate recovery of the components of the reaction herein, they can be dissolved in an inert solvent such as ethylene glycol, diethylene glycol monomethyl ether, acetone, etc.

In the reaction zone the contents thereof are then maintained at an elevated temperature and elevated pressure for a time sufficient to convert methanol to acetaldehyde. Pressures which are suitable for use herein generally are above about 1000 pounds per square inch gauge (6.83 MPa), but should not be in excess of about 10,000 pounds per square inch gauge (68.30 MPa). An especially desirable pressure range is from about 1000 pounds per square inch gauge (6.83 MPa) to about 6000 pounds per square inch gauge (40.98 MPa), preferably from about 2000 pounds per square inch gauge (13.66 MPa) to about 5000 pounds per square inch gauge (34.15 MPa). Temperatures which are suitable for use herein are those temperatures which initiate a reaction between the reactants herein to selectively produce acetaldehyde, generally from about 150° C. to about 250° C., preferably from about 175° C. to about 225° C. The reaction is conducted for a time period sufficient to convert methanol to acetaldehyde, normally from about 0.5 hour to about 10 hours, especially from about one to about five hours.

Recovery of the desired acetaldehyde from the reaction product can be effected in any convenient or conventional manner, for example, by distillation. At ambient pressure and about 21° C., the components will distill off in the following sequence for the desired recovery: dimethyl ether, acetaldehyde, methyl acetate, methanol and ethanol.

It is to be noted that the catalyst system herein is highly selective to the formation of acetaldehyde and minimizes the formation of undesirable by-products such as alcohols, ethers, esters and other alcohol derivatives.

DESCRIPTION OF PREFERRED EMBODIMENTS

The following Examples and Tables serve to further illustrate and instruct one skilled in the art the best mode of how to practice this invention and are not intended to be construed as limiting thereof.

The reactions herein were performed in a stainless steel pressure-resistant autoclave equipped with agitation means, for example, a type 316 stainless steel, 300 cc. autoclave marketed commercially by Autoclave Engineers. The methanol, hydrogen, carbon monoxide, cobalt acetylacetonate, iodine promoter and arsenic or antimony-base ligand were introduced into the autoclave. The autoclave was connected to another larger reservoir containing synthesis gas (hydrogen and carbon monoxide) which fed said synthesis gas into the steel autoclave at a set pressure on demand. Thus, the reactor pressure was maintained throughout the course of the reaction. The reaction pressure and temperature were adjusted to operating conditions and the mixture reacted for a period of time sufficient to produce acetaldehyde.

EXAMPLES I-V

Into a 300 cc. stainless steel autoclave were charged three millimoles of cobalt acetylacetonate, 0.75 millimole of iodine, three millimoles of the defined arsenic or antimony base ligand and 100 milliliters of methanol (see Table I). The reactor was next purged twice with nitrogen gas and then pressurized witn synthesis gas ($H_2:CO=1$) to a pressure of about 1000 pounds per square inch gauge (6.83 MPa) lower than the desired working pressure. The system was then heated to a temperature of about 200° C., and the pressure was adjusted to a working pressure of about 4000 pounds per square inch gauge (27.6 MPa). The reaction was allowed to proceed for approximately three hours, after which the reactor was cooled by an internal cooling coil to about $-75°$ C. The reactor was vented through a dry gas meter and a gas sample was taken for a mass spectral analysis, and the liquid product was analyzed using a Model 900 Perkin-Elmer gas chromatograph utilizing a 16 ft. (4.88 meters)×1.8 in. (0.32 centimeter) stainless steel column wherein eight ft. (2.44 meters) of the column was packed with 80/100 mesh Poropak Q and the other eight ft. (2.44 meters) was packed with 80/100 mesh Poropak R. Poropak Q and Poropak R are polyvinyl benzene type resins which are marketed commercially by Waters Associates, a corporation located in Milford, Massachusetts. The gas chromatograph was programmed to increase from 40° C. to 190° C. at a rate of 32° C./min. and with a helium flow rate of 30 cc./min. The above procedure was followed in the Examples set forth in Table I below.

TABLE I

| Example No. | Catalyst System | Percent MeOH[a] Conv. | Mole Percent Selectivity | | | | |
|---|---|---|---|---|---|---|---|
| | | | $Me_2O$[b] | AcH[c] | EtOH[d] | MeOAc[e] | Other[f] |
| I | Cobalt acetylacetonate + iodine + tri-phenyl arsine | 60.5 | 5.4 | 56.5 | 16.7 | 13.1 | 8.3 |
| II | Cobalt acetylacetonate + iodine + di-phenyl, methyl arsine | 66.3 | 3.6 | 46.8 | 19.6 | 16.8 | 13.2 |
| III | Cobalt acetylacetonate + iodine + di-methyl, phenyl arsine | 41.8 | 5.0 | 39.7 | 32.7 | 15.5 | 7.1 |
| IV | Cobalt acetylacetonate + iodine + tri-p-tolyl arsine | 52.4 | 33.2 | 38.1 | 10.4 | 12.0 | 6.3 |
| V | Cobalt acetylacetonate + iodine + tri-phenyl stibine | 47.4 | 18.5 | 40.6 | 10.8 | 10.8 | 19.3 |

[a]MeOH = Methanol
[b]$Me_2O$ = Dimethyl ether
[c]AcH = Acetaldehyde
[d]EtOH = Ethanol
[e]MeOAc = Methyl acetate
[f]Other = Mixtures of ethyl acetate, methyl formate, propanols, propionaldehyde, butanols, n-butyraldehyde and methane As can readily be determined from the above data, the catalyst system herein is selective to acetaldehyde formation under the specified reaction conditions.

In each of Examples VI to VIII the procedure of Examples I to V was followed. However, in Example VI triethyl arsine was used in place of a required arsenic base ligand. In Example VII tri-phenyl bismuth, a ligand similarly falling outside the scope of an arsenic or antimony base ligand required herein, was used. In Example VIII tri-phenyl phosphine, also falling outside the scope of an arsenic or antimony base ligand, and an additional compound, ruthenium acetylacetonate, were used. The results are tabulated below in Table II.

TABLE II

| Example No. | Catalyst System | Percent MeOH[a] Conv. | Mole Percent Selectivity | | | | |
|---|---|---|---|---|---|---|---|
| | | | $Me_2O$[b] | AcH[c] | EtOH[d] | MeOAc[e] | Other[f] |
| VI | Cobalt acetylacetonate + iodine + tri-ethyl arsine | 60.7 | 2.4 | 24.1 | 48.0 | 17.9 | 7.6 |
| VII | Cobalt acetylacetonate + iodine + tri-phenyl bismuth | 70.0 | 5.8 | 14.1 | 44.1 | 15.3 | 20.7 |
| VIII | Cobalt acetylacetonate + iodine + tri-phenyl phosphine + ruthenium acetylacetonate | 48.1 | 7.0 | None | 58.2 | 18.4 | 16.4 |

[a]MeOH = Methanol
[b]$Me_2O$ = Dimethyl ether
[c]AcH = Acetaldehyde
[d]EtOH = Ethanol
[e]MeOAc = Methyl acetate
[f]Other = Mixtures of ethyl acetate, methyl formate, propanols, propionaldehyde, butanols, n-butyraldehyde and methane The above clearly shows the criticality of the catalyst system used herein for the production of acetaldehyde. In each of Examples VI to VIII ethanol was the predominant compound produced. In each of Examples VI and VII the amount of desired acetaldehyde was far less than that obtained in Examples I to V. In Example VIII no acetaldehyde was produced.

The following shows that in order to obtain improved acetaldehyde yields the molar ratio of iodine to cobalt introduced into the reaction zone is critical.

EXAMPLES IX–XV

Into a 300 cc. stainless steel autoclave were charged three millimoles of cobalt acetylacetonate, the designated concentration of iodine, three millimoles triphenyl arsine and 100 milliliters of methanol. The reactor was next purged twice with nitrogen gas and then pressurized with synthesis gas ($H_2$:CO = 1) to a pressure of about 1000 pounds per square inch gauge (6.83 MPa) lower than the desired working pressure. The system was then heated to a temperature of about 200° C., and the pressure was adjusted to a working pressure of about 4000 pounds per square inch gauge (27.6 MPa). The reaction was allowed to proceed for approximately three hours, after which the reactor was cooled by an internal cooling coil to about −75° C. The reactor was vented through a dry gas meter and a gas sample was taken for a mass spectral analysis, and the liquid product was analyzed using a Model 900 Perkins-Elmer gas chromatograph utilizing a 16 ft. (4.88 meters)×1.8 in. (0.32 centimeter) stainless steel column wherein 8 ft. (2.44 meters) of the column was packed with 80/100 mesh Poropak Q and the other 8 ft. (2.44 meters) was packed with 80/100 mesh Poropak R. Poropak Q and Poropak R are polyvinyl benzene type resins which are marketed commercially by Waters Associates, a corporation located in Milford, Massachusetts. The gas chromatograph was programmed to increase from 40° C. to 190° C. at a rate of 32° C./min. and with a helium flow rate of 30 cc./min. The above procedure was followed in the Examples set forth in Table III as follows.

TABLE III

| Example | [Co][1] | [I][2] | I/Co[3] | Percent Acetaldehyde Yield[4] |
|---|---|---|---|---|
| IX | 0.06 | 0 | 0 | 0.0 |
| X | 0.06 | 0.0075 | 1:8 | 20.1 |
| XI | 0.06 | 0.015 | 1:4 | 34.2 |
| XII | 0.06 | 0.030 | 1:2 | 12.1 |
| XIII | 0.06 | 0.060 | 1:1 | 12.2 |
| XIV | 0.06 | 0.120 | 2:1 | 10.7 |
| XV | 0.06 | 0.300 | 5:1 | 4.9 |

[1][Co] Cobalt molar concentration as Co
[2][I] Iodine molar concentration as I
[3]I/Co Iodine-cobalt molar ratio
[4]Percent acetaldehyde yield = [percent methanol conversion × mole percent acetaldehyde selectivity]/100

EXAMPLES XVI to XX

The procedure of Examples IX to XV was followed with the exception that triphenyl stibine was substituted for the triphenyl arsine. The results are set forth below in Table IV.

TABLE IV

| Example | [Co][1] | [I][2] | I/Co[3] | Percent Acetaldehyde Yield[4] |
|---|---|---|---|---|
| XVI | 0.06 | 0.0075 | 1:8 | 0.0 |
| XVII | 0.06 | 0.015 | 1:4 | 9.5 |
| XVIII | 0.06 | 0.030 | 1:2 | 12.0 |
| XIX | 0.06 | 0.060 | 1:1 | 6.5 |
| XX | 0.06 | 0.180 | 3:1 | 4.4 |

[1][Co] Cobalt molar concentration as Co
[2][I] Iodine molar concentration as I
[3]I/Co Iodine-cobalt molar ratio
[4]Percent acetaldehyde yield = [percent methanol conversion × mole percent acetaldehyde selectivity]/100

The data in Tables III and IV show that in order to obtain improved acetaldehyde yields the molar ratio of iodine to cobalt introduced into the reaction zone must be in the range of about 1:100 to about 2:1, preferably about 1:10 to about 1:2.

The following shows that other cobalt entities falling within the definitions set forth hereinabove will also produce acetaldehyde satisfactorily herein.

A number of runs was carried out following the procedure of Example I but with several exceptions. Instead of cobalt acetylacetonate, six millimoles of a different cobalt entity were used. The amount of tri-phenyl arsine was six millimoles and the amount of iodine 1.5 millimoles. The data obtained are summarized below in Table V.

TABLE V

| Example No. | Catalyst System | Percent MeOH[a] Conv. | Mole Percent Selectivity | | | | | |
|---|---|---|---|---|---|---|---|---|
| | | | Me$_2$O[b] | AcH[c] | EtOH[d] | MeOAc[e] | n-PrCHO[f] | Other[g] |
| XXI | Cobalt acetate [Co(OAc)$_2$] + iodine + tri-phenyl arsine | 57.8 | 14.0 | 32.2 | 12.0 | 18.3 | 16.6 | 6.9 |
| XXII | Cobalt oxide [Co$_3$O$_4$] + iodine + tri-phenyl arsine | 45.6 | 7.1 | 36.8 | 12.6 | 14.4 | 14.4 | 14.7 |
| XXIII | Cobalt sulfate [CoSO$_4$] + iodine + tri-phenyl arsine | 58.9 | 14.8 | 42.6 | 9.5 | 13.1 | 13.4 | 6.6 |
| XXIV | Cobalt carbonyl [Co$_2$(CO)$_8$] + iodine + tri-phenyl arsine | 48.9 | 10.5 | 52.5 | 6.0 | 10.0 | 10.4 | 10.6 |

[a]MeOH = Methanol
[b]Me$_2$O = Dimethyl ether
[c]AcH = Acetaldehyde
[d]EtOH = Ethanol
[e]MeOAc = Methyl acetate
[f]n-PrCHO = n-butyraldehyde
[g]Other = Mixtures of ethyl acetate, methyl formate, propanols, propionaldehyde, butanols and methane Obviously, many modifications and variations of the invention, as hereinabove set forth, can be made without departing from the spirit and scope thereof, and therefore only such limitations should be imposed as are indicated in the appended claims.

We claim:

1. A process for selectively producing acetaldehyde which comprises introducing into a reaction zone (1) methanol, (2) hydrogen, (3) carbon monoxide, (4) a cobalt entity selected from the group consisting of a cobalt carbonyl, a hydrido cobalt carbonyl and a cobalt-containing material convertible to a cobalt carbonyl or a hydrido cobalt carbonyl, (5) a ligand selected from the group consisting of an arsenic and antimony base ligands defined by the following formula:

wherein X is a member selected from the group consisting of trivalent arsenic or trivalent antimony: and R$_1$, R$_2$ and R$_3$ are either alike or different members selected from the group consisting of alkyl, phenyl and alkyl substituted phenyl radicals, with the provision that at least one R group is phenyl or alkyl substituted phenyl, and (6) an iodine compound and then subjecting the contents of said reaction zone to an elevated temperature and an elevated pressure for a time sufficient to convert methanol to acetaldehyde, the cobalt entity and the ligand entity being present in a molar ratio of about 20:1 to about 1:10, the cobalt entity and the iodine entity being present in a molar ratio of about 100:1 to about 1:2, the weight percent of combined cobalt entity, ligand entity and iodine entity being about 0.01 to about 10, based on methanol, the carbon monoxide and hydrogen being present in a molar ratio of about 1:10 to about 10:1, the reaction temperature being about 150° to about 250° C., the reaction pressure being about 1000 to about 10,000 pounds per square inch gauge and the reaction period being about 0.5 to about 10 hours.

2. The process of claim 1 wherein the ligand is tri-phenyl arsine.

3. The process of claim 1 wherein the ligand is di-phenyl methyl arsine.

4. The process of claim 1 wherein the ligand is dimethyl phenyl arsine.

5. The process of claim 1 wherein the ligand is tri-p-tolyl arsine.

6. The process of claim 1 wherein the ligand is tri-phenyl stibine.

7. The process of claim 1 wherein the cobalt entity is cobalt acetylacetonate.

8. The process of claim 1 wherein the cobalt entity is cobalt acetate.

9. The process of claim 1 wherein the cobalt entity is cobalt oxide.

10. The process of claim 1 wherein the cobalt entity is cobalt sulfate.

11. The process of claim 1 wherein the cobalt entity is cobalt carbonyl.

12. The process of claim 1 wherein the iodine compound is a member selected from the group consisting of iodine, potassium iodide, calcium iodide, sodium iodide, lithium iodide, hydrogen iodide, methyl iodide and ethyl iodide, or mixtures thereof.

13. The process of claim 1 wherein the iodine promoter is iodine.

14. The process of claim 1 wherein the cobalt entity and the arsenic or antimony base ligand are present in a molar ratio of about 10:1 to about 1:5.

15. The process of claim 1 wherein the cobalt entity and the iodine entity are present in a molar ratio of about 10:1 to about 1:1.

16. The process of claim 1 wherein the weight percent of the combined cobalt, arsenic or antimony and iodine is in the range of about 0.1 to about five percent.

17. The process of claim 1 wherein the reaction temperature is about 175° C. to about 225° C.

18. The process of claim 1 wherein the reaction pressure is about 1000 pounds per square inch gauge to about 6000 pounds per square inch gauge.

19. The process of claim 1 wherein the reaction pressure is about 2000 pounds per square inch gauge to about 5000 pounds per square inch gauge.

20. The process of claim 1 wherein the reaction time is about one to about five hours.

21. The process of claim 1 wherein the molar ratios of carbon monoxide to hydrogen are about 1:10 to about 10:1.

22. The process of claim 1 wherein the molar ratios of carbon monoxide to hydrogen are about 1:3 to about 3:1.

* * * * *